United States Patent [19]

Mayhan et al.

[11] Patent Number: 4,863,445
[45] Date of Patent: Sep. 5, 1989

[54] ASSEMBLY FOR INHIBITING MICROBIAL GROWTH IN COLLECTED FLUID

[75] Inventors: Kenneth G. Mayhan, Irvine; Bernice I. Romo, Alhambra; Robert L. Murtfeldt, Redondo Beach; William J. Bertrand, Sunnymeade, all of Calif.

[73] Assignee: Baxter Travenol Laboratories, Inc., Del.

[21] Appl. No.: 635,772

[22] Filed: Jul. 30, 1984

[51] Int. Cl.[4] .............................................. A61M 1/00
[52] U.S. Cl. ..................................... 604/317; 604/322
[58] Field of Search ................... 604/317, 82, 83, 890, 604/49, 50, 322-329, 359, 360, 892, 894; 422/29, 28; 423/584; 424/16, 17, 14, 19, 21

[56] References Cited

U.S. PATENT DOCUMENTS

| | | | |
|---|---|---|---|
| 1,262,589 | 4/1918 | Liebknecht | 423/584 |
| 3,851,648 | 12/1974 | Brooke | 604/892 |
| 3,856,932 | 12/1974 | May | 424/16 |
| 3,926,188 | 12/1975 | Baker et al. | 604/294 |
| 4,217,898 | 8/1980 | Theeuwes | 604/893 |
| 4,233,263 | 11/1980 | Schaeffer | 604/322 |
| 4,259,383 | 3/1981 | Eggensperger et al. | 422/29 |
| 4,363,322 | 12/1982 | Andersson | 604/359 |
| 4,445,889 | 5/1984 | Wong et al. | 604/317 |
| 4,519,801 | 5/1985 | Edgren | 604/890 |
| 4,525,340 | 6/1985 | Lange et al. | 604/890 |

Primary Examiner—C. Fred Rosenbaum
Assistant Examiner—Mario Costantino
Attorney, Agent, or Firm—Paul C. Flattery; Roger A. Williams

[57] ABSTRACT

An assembly for inhibiting microbial growth in collected body fluid includes a reservoir for collecting the fluid, and a tablet in the reservoir, which tablet dissolves in the collected fluid to produce hydrogen peroxide in an amount sufficient to inhibit microbial growth in the collected fluid. The tablet is partially coated with an insoluble coating which leaves a portion of the tablet uncoated to provide a constant surface area exposed to the collected body fluid, which surface area is of a size to provide sufficient hydrogen peroxide for inhibition of microbial growth.

25 Claims, 5 Drawing Sheets

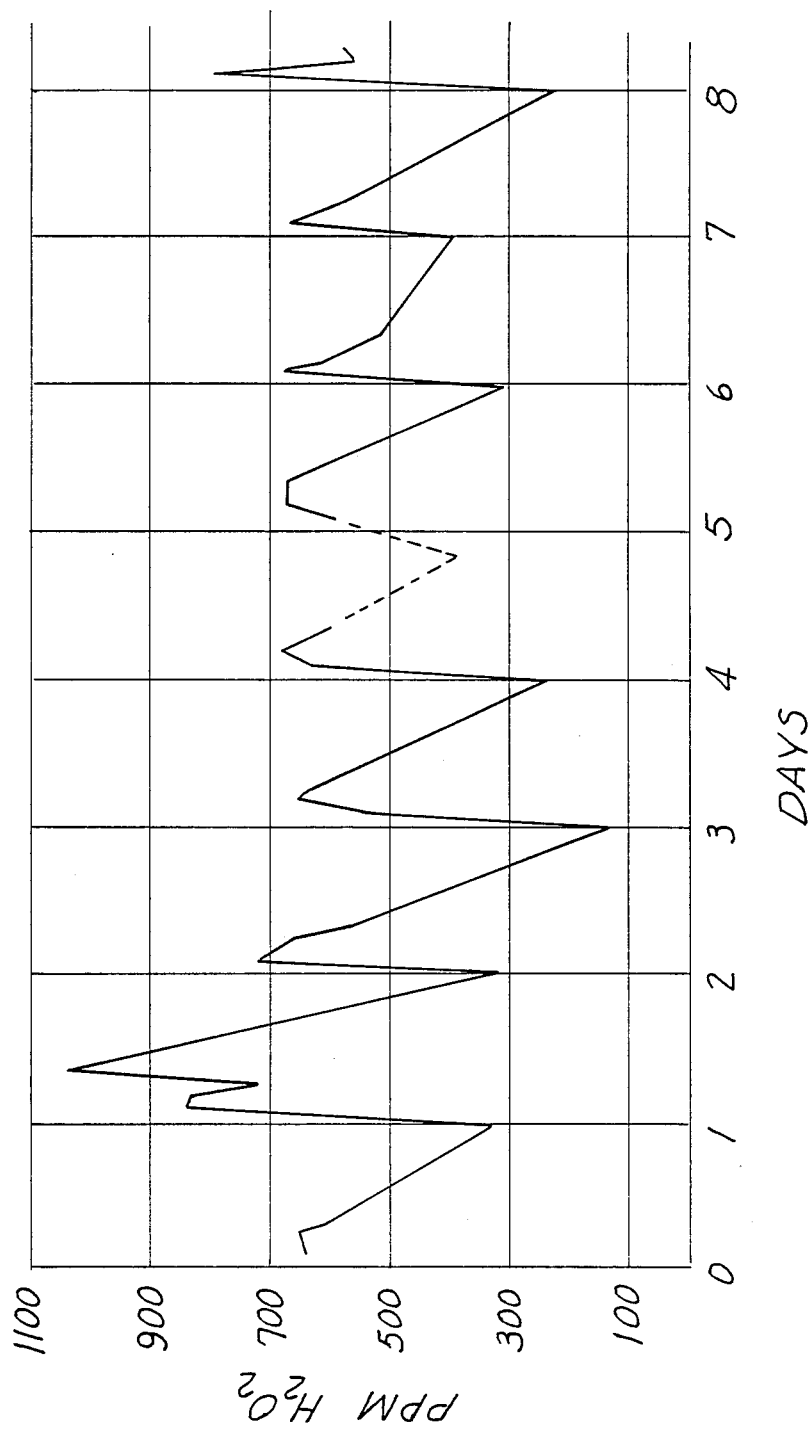

ASSEMBLY FOR INHIBITING MICROBIAL GROWTH IN COLLECTED FLUID

BACKGROUND OF THE INVENTION

The invention herein is directed to an assembly for collecting body fluid and storing the collected body fluid. The assembly provides the inhibition of microbial growth in the collected body fluid. More particularly, the invention herein is directed to an assembly for collecting body fluids, such as urine, and for inhibiting or killing microbes which can be present in the collected body fluid by creating a bacteristatic or bactericidal presence in the collected body fluid.

In the medical field, there are many devices which are can used to collect body fluids from a patient. Such devices include urinary drainage bags, suction canisters, ostomy bags, wound drainage reservoirs, and the like. The presence of collected body fluids in such containers creates an environment especially adapted for bacterial growth. The collected body fluid provides a media for the growth of microbes, such as bacteria. Microbial growth in collected body fluid is undesirable as the presence of microorganisms can lead to infection of the patient or can lead to infection of other patients through transfer of the microbes by cross contamination and nosocomial infections. Body fluids which enter a collection device can be contaminated with microbes due to a patient's infection prior to collection. For example, some patients which have urinary tract infection can pass urine with a high bacterial load into the drainage bag. Such bacterial loads can be as great as $10^5$ counts per milliliter. In patients not having a pre-infection, fluids collected are generally essentially sterile. However, the collection device can become contaminated during emptying or while sampling through the sampling or emptying ports provided on the collection device due to touch or aerosol contamination. During such procedures, a cross-contamination of urinary drainage bags can occur and thereby increase the risk of nosocomial infections to both patients and nurses. The presence of nosocomial infection increases hospital costs by lengthening average patient stays, by increasing amounts of antimicrobial prophylaxis used, and by increasing laboratory diagnostic testing of affected patients. Bacterial infections are also undesirable as they can lead to patient discomfort, additional patient treatment, additional illness, and in same instances, death.

It would, therefore, be desirable to provide an assembly for collecting body fluids from a patient which would provide an inhibition and/or killing of microbes which can be present in the collected fluid within the assembly. It would be desirable to provide an assembly which would have an inhibiting or killing effect on microbes in the collected body fluid, regardless of whether such microbes entered the collection reservoir in the body fluid or through contamination from the surrounding environment. One such attempt to provide such an assembly is described in U.S. Pat. No. 4,233,263 of Northwestern University. The assembly therein provides for the introduction of hydrogen peroxide to the collection reservoir prior to the collection of urine from a patient. The patent teaches that hydrogen peroxide in the reservoir provides an effective inhibition of bacterial growth in the reservoir. However, a drawback and disadvantage of the assembly is that there is a need to constantly attend the drainage assembly to add the liquid hydrogen peroxide prior to each accumulation of a volume of urine. Such constant attention by a nurse is time consuming and nursing time is a valuable commodity on a post-operative, intensive care, or other medical ward.

It would be desirable to provide an assembly which could provide an inhibition or killing of microbes in a collected body fluid, but which would not need to be attended and which would provide such activity for the length of time that such body fluid is to be collected.

SUMMARY OF THE INVENTION

The invention herein is directed to a body fluid collection reservoir which can provide an inhibition of microbial growth in the body fluid collected within the reservoir. More particularly, the invention herein is directed to a urinary drainage bag assembly which is designed to drain and collect urine from a patient and which inhibits microbial growth in the collected urine within the drainage bag by providing a bacteristatic and bactericidal activity in the collected fluid.

The body fluid collection assembly herein includes a reservoir for receiving the body fluid. Within the reservoir is at least one tablet which is capable of dissolving to form hydrogen peroxide when body fluid enters the reservoir. That is, the tablet dissolves in the body fluid to produce hydrogen peroxide in an effective amount sufficient for inhibiting and/or killing microbes present in the body fluid. The tablet is designed such that it contains sufficient material to provide hydrogen peroxide over the time period the assembly is anticipated to be connected to the patient for receiving the body fluid. The tablet is also partially coated with an insoluble coating such that a predetermined surface area remains uncoated. The uncoated surface area is of a size sufficient to provide sufficient hydrogen peroxide upon dissolving of the tablet material in the body fluid to inhibit and/or kill microbes which can be present in the body fluid. The tablet is designed such that the surface area remains substantially constant during the time that the tablet remains in the body fluid collected in the assembly and the assembly is connected to a patient.

The tablet is a tablet containing a hydrogen peroxide releasing compound. Various hydrogen peroxide releasing compounds are available. For example, the tablet can be made from hydrogen peroxide releasing compounds selected from the group of compounds such as sodium perborate, sodium carbonate, urea peroxide, and oxone peroxymonosulfate. The tablet can contain a small amount of a release agent which assists in the tableting of the compound by permitting the compound, once tableted, to be easily removed from the tablet mold. Acceptable release agents can be stearic acid, zinc stearate, magnesium stearate, and sodium benzoate.

In addition to the release agent, the tablet can contain a binding compound which assists in holding the tablet together. Acceptable binding agents include polyvinylpyrrolidone, magnesium silicate, and methylcellulose. The tablet can also contain a bufferng agent which will tend to provide the proper pH in the collected body fluid. For example, when the tablet is used in a urinary drainage bag, a buffer can be used which will provide a pH of about pH 7.

The insoluble coating on the tablet covers the tablet except for one surface area. For a generally cylindrical tablet, the coating extends around the cylindrical sidewall and can cover one of the circular end surfaces of the tablet. That is, the tablet can have either one wall or both of its circular end walls noncoated. Acceptable coatings can be any coating which is insoluble in the body fluid to be collected. It is preferred to use thermoplastic coatings or thermosetting coatings. Acceptable coatings include nitrocellulose base lacquer, epoxy coatings, urethane, cellulose acetate, silicone, vinyl, and methacrylate.

Rather than coating the tablet, the tablet can be formed in a preformed cup or tube. When the tablet is formed in a tube or cup, the cup or tube can be constructed of a low density polyethylene, polymethylmethacrylate, polypropylene and polycarbonate. Such materials provide the necessary insolubility, but also permit a good bond between the formed tablet and the sidewalls of the tube or cup as to maintain the open surface area as the only area of contact with the body fluid once the tablet is placed in a body fluid collection reservoir. The compounds which can be used to form a cup also can be used as coatings on formed tablets.

BRIEF DESCRIPTION OF THE DRAWINGS

FIG. 8 is a plot of a curve illustrating the effective $H_2O_2$ upon dissolution of a tablet.

DETAILED DESCRIPTION

Figure 2:
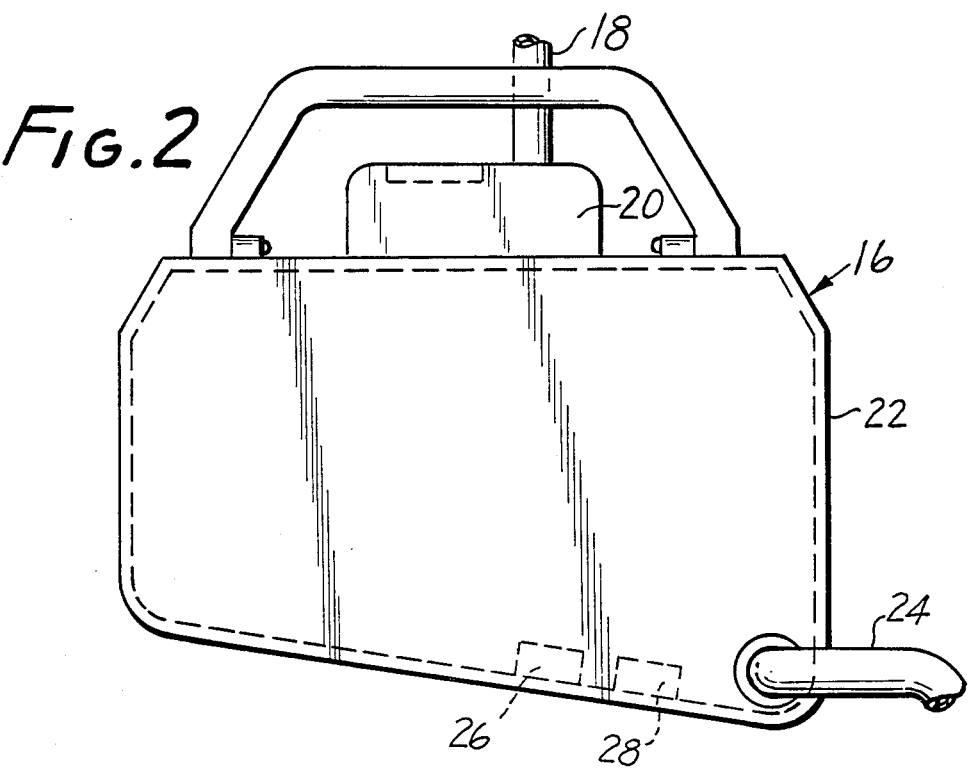
FIG. 2 is a lateral view of a urinary drainage bag assembly illustrating a use of the invention herein.

The body fluid collection reservoir herein which provides antimicrobial activity in the collected body fluid within the reservoir will be described with regard to the accompanying drawings. With regard to FIG. 2, a body fluid collection assembly is illustrated. The assembly shown in FIG. 2 is a representation of a urinary drainage bag 16 for collecting urine drained from a patient's urinary tract. Although the invention herein will be described with regard to a urinary drainage bag assembly, it is not meant to be limited to such an application as the invention herein can be useful in any assembly which collects body fluid drained from a patient. For example, the invention can be used in urinary drainage bags, suction canisters, ostomy bags, wound drainage reservoirs, and reservoir devices for collecting blood, respiratory mucus, saliva, G.I. tract fluid, bile, spinal fluid, lymphatic fluid, fluid from the peritoneal cavity, and the like.

The body fluid collection assembly includes a drainage bag 16 which is connected to a patient through a catheter 18 which is partially shown in FIG. 2. The catheter 18 can be any standard and commercially available urinary drainage catheter, many of which are commonly referred to as Foley urinary drainage catheters. The catheter can lead into a drip chamber 20 on the urinary drainage bag. The drainage bag itself can be constructed of any material. For example, some drainage bags have flexible sidewalls and other drainage bags have rigid sidewalls. The particular sidewall configuration and structure does not form a part of the invention herein, and any body fluid collection reservoir can be utilized in the practice of the invention herein. The drainage bag is provided with an outlet or drain 24 through which collected body fluid can be removed either to empty the bag or for obtaining samples from the body fluid within the reservoir.

Placed in the reservoir of the body fluid collection assembly is a tablet 26 which is constructed from a composition which dissolves to produce hydrogen peroxide upon encountering the body fluid. In a preferred working embodiment, two tablets 26 and 28 were provided to provide sufficient hydrogen peroxide in the collected body fluid (urine) to provide antimicrobial activity for up to seven days. The number of tablets provided in the reservoir will depend upon the size of the tablets, the available surface area on each tablet for exposure to the body fluid to produce hydrogen peroxide, and the length of time that it is desired to provide antimicrobial activity to the collected body fluid.

Figure 1:
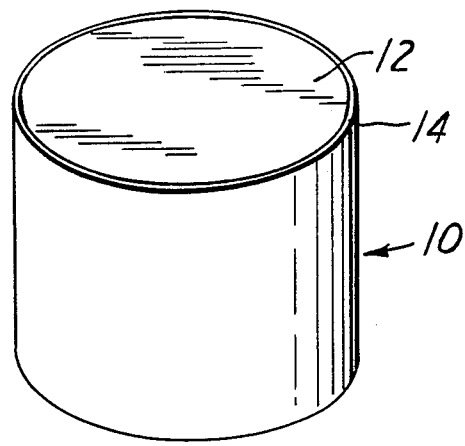
FIG. 1 is a perspective view of a partially coated tablet which can be placed in a body fluid collection reservoir to provide antimicrobial activity therein.

A tablet which can be used herein is shown in FIG. 1. The tablet 10 includes a hydrogen peroxide producing composition 12. The hydrogen peroxide producing composition can be any such composition which upon encountering the body fluid, produces hydrogen peroxide. Suitable compositions include sodium perborate, sodium percarbonate, urea peroxide, oxone peroxymonosulfate, and the like. In the preferred embodiment, sodium perborate has been found to provide beneficial properties such that it can be tableted in sufficient quantity to provide a tablet having sufficient strength to provide, upon dissolving in urine, an antimicrobial activity for up to seven to ten days. The composition 12 can include acceptable release agents which permit the tablet to be stripped from a tablet making mold. Such release agents permit the removal of the formed tablet from its mold without unnecessary pressure and without fracturing the formed tablet. Acceptable release agents include boric acid, sodium benzoate, magnesium stearate, zinc stearate and stearic acid. A preferred release agent for use with the preferred hydrogen peroxide producing composition of sodium perborate is magnesium stearate.

The tablet is constructed of a hydrogen peroxide producing composition such that it will provide hydrogen peroxide in the body fluid, upon dissolving, over a desired period of time, depending upon the use of the body fluid drainage assembly. For example, in urinary drainage bag collection assemblies, an acute care patient in a medical ward is generally catheterized for up to seven days. In such instances, it would be desirable to provide a tablet which would slowly release hydrogen peroxide into the collected urine over the seven day period to effectively provide antimicrobial activity in the collected urine while the patient remains catheterized. Some patients in ICU, neurological, and orthopedic wards can be catheterized for periods longer than seven days. The mere providing of a tablet of a hydrogen peroxide generating material would not provide the desired results of effective antibacterial (antimicrobial) activity over the catheter indwelling time. For example, if a tablet of sodium perborate were introduced into a urinary drainage bag, the tablet would begin to dissolve and produce hydrogen peroxide. As the tablet dissolves, its size decreases and less surface area becomes available for dissolving additional sodium perborate. Thus, there would be a diminishing release of hydrogen peroxide over time. It is desirable to provide a slow, steady release of hydrogen peroxide such that a sufficient antimicrobial amount of hydrogen peroxide remains in the collected body fluid. It is desirable to provide a tablet which provides $H_2O_2$ in an amount from about 0.03% to about 0.15% by weight and preferably about 0.1% $H_2O_2$ as such an amount has been found to be sufficient to produce a bactericidal effect in urine. Amounts less than 0.03% can be used, but do not produce a quick kill or inhibition of bacteria. Amounts greater than 0.15% can be used, but such amounts do not provide any significantly better benefits than 0.15% and greater amounts can lead to cloudiness in collected urine.

It has been found herein that a tablet can be provided which provides a slow, yet effectively constant rate of delivery of hydrogen peroxide. Such a tablet is a partially coated tablet as shown in FIG. 1. The tablet 10 is partially coated with an insoluble coating 14. Any coating material can be used to coat the tablet as long as the material is insoluble to the body fluid to be collected. Preferred coatings for the tablet have been found to be thermoplastic materials, although some thermoset coatings can be used. A drawback with the use of thermoset coatings is that the materials can be exothermic and give off heat as they form. The generation of heat can be undesirable for a hydrogen peroxide generating composition as the composition can become unstable. Therefore, it is desirable to use a thermoplastic coating, if possible. Acceptable coatings can be provided using nitrocellulose base lacquer, epoxy coatings, urethane, cellulose acetate, polyethylene, polymethylmethacrylate, polypropylene, polycarbonate, vinyl, and the like.

In the preferred embodiment for a cylindrical tablet, the coating is provided on the cylindrical sidewall and on one circular end wall of the cylindrical tablet. The remaining circular end wall is left uncoated to provide a surface which can be exposed to the body fluid which, upon encountering the body fluid, can dissolve to provide hydrogen peroxide. The partial encapsulation of the tablet leaving only one circular face exposed to the body fluid provides a tablet which will always have a constant surface area exposed to the solvating properties of the body fluid. Therefore, there is an essentially constant rate of hydrogen peroxide production due to the static surface area exposed to the body fluid.

For a cylindrical tablet, both circular end walls can be left uncoated. Thus, an effective surface area for producing hydrogen peroxide is the combined surface areas of the two uncoated circular ends.

The tablet can also be formed in a preformed cup or tube of the insoluble material. The use of a preformed cup or tube still leaves an exposed surface area of the hydrogen peroxide producing active ingredient when the tablet is placed in the drainage reservoir assembly.

In selecting the insoluble coating material, a material is selected which will interact with the hydrogen peroxide generating material to form a bond at the interface between the two materials. It is important that such a bonding occur, whether the bonding be a chemical bonding or a physical bonding of the two materials. The bonding is important in that it substantially inhibits or prevents the body fluid from flowing between the coating and the tablet. If the body fluid were permitted to flow between the tablet and coating, then the surface area of the hydrogen peroxide producing material exposed to the body fluid would be increased and the ability to release hydrogen peroxide at a substantially constant rate would be destroyed.

Figure 3:
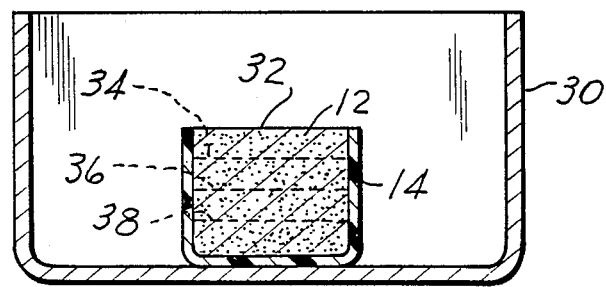
FIG. 3 is a partial cross-sectional view of a body fluid collection reservoir and tablet illustrating the dissolution of the tablet in a collected body fluid.

The effects of the dissolving of the tablet is best illustrated with regard to FIG. 3. In FIG. 3, the tablet 10 is shown in cross section with a rather somewhat enlarged outer coating 14. In a working embodiment of the tablet, the outer coating 14 is approximately from about 0.003 to 0.010 inches and preferably about 0.005 inches in thickness, although the thickness is not critical. Initially, the tablet 12 is exposed as its upper uncoated surface 32 to the body fluid which can collect in the reservoir defined by the sidewall 30. The insoluble coating 14 protects the remaining surface area of the tablet from the solvent effect of the body fluid. As the tablet dissolves, a subsequent lower surface 34 as indicated by the dashed line in FIG. 3 is exposed to the body fluid. Such a lower surface 34 is substantially the same surface area as the original exposed surface 32. As the tablet continues to dissolve, still another surface 36 is exposed as shown by the dashed line 36 in FIG. 3 and again subsequently the tablet can dissolve to expose surface 38. All of the surfaces 32, 34, 36 and 38 are of substantially the same surface area. Therefore, the composition comprising the tablet as it dissolves provides a constant rate production of hydrogen peroxide in the body fluid contained in the reservoir.

The tableting system that is the subject of the invention herein uses a tablet which provides hydrogen peroxide upon dissolving in the body fluid. The tablet contains sufficient material for providing an effective hydrogen peroxide concentration in the body fluid to inhibit the growth of microbes. The amount of material in each tablet depends upon the end use of the system. For example, in a urinary drainage bag system which is intended to be connected to a patient for 5 to 7 days, the tablet contains sufficient material to generate hydrogen peroxide over the 5 to 7 day period. In a suction canister system which could be used or which anticipated use is for one day, the tablet contains sufficient material for releasing hydrogen peroxide over the one day period.

It has been found herein that for a urinary drainage bag system with an intended use for 5 to 7 days that it is preferred to provide two tablets which introduce hydrogen peroxide to the collected urine. Two tablets provide sufficient material and can be constructed to provide an adequate surface area that a constant rate of hydrogen peroxide production can be achieved over the 5 to 7 day period. In a preferred embodiment of the assembly for use in urinary drainage, 20 grams of sodium perborate were found to be sufficient to provide effective inhibition of microbial growth in urine for up to 7 days. In order to provide the 20 grams of sodium perborate in a tablet and which would have an exposed surface area to provide effective amounts of hydrogen peroxide, it was determined that an effective surface area would be 1.57 square inches. For a single tablet to provide 1.57 square inches, the tablet would need to be 1.414 inches in diameter. The tablet would also need to be aobut one-half inch in height to be able to include 20 grams. However, it is difficult to compact a tablet having such dimensions. It was, therefore, determined that by using two tablets the same effective surface area could be obtained and the tablets could be more readily constructed. Thus, two tablets one inch in diameter would provide 0.785 square inches in surface area for a total surface area of 1.57 square inches between the two tablets. Each tablet is constructed such that it contains about 10 grams of sodium perborate.

It has also been found that it is difficult to compress and tablet sodium perborate. It is, therefore, desirable to add to the composition a release agent which assists in the removal of the formed tablet from the tablet mold. For a tablet containing 10 grams, at least 90% to 95% of the tablet can be the hydrogen peroxide producing agent, such as sodium perborate, while the remaining percent by weight can be a release agent, such as sodium benzoate, boric acid, stearic acid, zinc stearate, or magnesium stearate.

In addition to incorporating a release agent in the tableting mixture, a binding agent can be added. A binding agent assists in binding the tablet together and prevents crumbling of the tablet. Acceptable binding agents include polyvinylpyrrolidone, magnesium silicate, and methylcellulose.

The tablet can be formed in a conventional tableting process wherein the material is inserted into a mold and a pressure exerted on the mold, along with any desired release agent and binding agent which can be intermixed with the $H_2O_2$ generating material, to compress the powdery material to form the tablet. In such a tablet molding operation, it has been found herein that for sodium perborate a preferred pressure of between 10,000 and 16,000 pounds per square inch can be used to form the 10 gram tablet. Pressures less than 10,000 psi provide a crumbly tablet whereas pressures greater than about 16,000 psi can tend to fracture the tablet. In a preferred method of forming the tablet, the sodium perborate is granulated by mixing the sodium perborate with a suitable volatile solvent, such as isopropyl alcohol. To the mixture is added polyvinylpyrrolidone as a binding agent and magnesium stearate as a release agent. The mixture is thoroughly mixed to form a pasty-like substance. The alcohol is evaporated, leaving a cake of the granulated sodium perborate mixture. The cake can be crumbled and broken to provide material for introduction to the mold cavity. The material, when compressed, at up to about 24,000 psi provides a tightly packed non-crumbly, one inch diameter tablet suitable for use in the invention herein. The composition of the tablet is such that at least 9.3 grams of the 10 gram tablet is the sodium perborate.

The tablets, once formed, are coated with an insoluble coating such as a nitrocellulose base lacquer, a vinyl, a methylmethacrylate, or a polymethylmethacrylate. The coatings can be applied using various coating techniques such as by spraying, dipping, roller coating, and the like. It is desirable to leave one flat end surface of the tablet exposed, which for each one inch tablet provides 0.785 square inches of surface area exposed for dissolving in urine or the appropriate body fluid.

The efficacy of the system herein and the ability of the tablets to provide a constant rate of hydrogen peroxide production in a body fluid was evaluated in studies wherein hydrogen peroxide generating tablets were placed in simulated urine. The following examples are illustrative of the tests that were undertaken to develop a substantially constant rate of hydrogen peroxide production from the tablets.

EXAMPLE I

Preparation of Simulated Urine

A simulated urine was prepared by mixing in a large flask 500 milliliters of water, 3.415 grams of sodium chloride, 3.4 grams of $KH_2PO_4$, and the pH was adjusted by the addition of $NH_4OH$ to provide a pH of about 6.5 (about 0.5 milliliters of ammonium hydroxide). To the solution was added 0.03 grams of creatine, 0.54 grams of creatinine, 0.02 grams albumin, and 7.58 grams of urea. The resultant mixture was filtered through a sterile filter and the filtrate collected in a sterile flask. The simulated urine was inoculated to determine if it could support bacterial growth. The filtrate was inoculated with 5 milliliters of an E. coli ATCC strain 26 culture in trypticase soya broth (TSB). The inoculum contained about $10^7$ organisms per milliliter. Nine milliliters of the simulated urine was placed in two separate test tubes and one test tube was inoculated with about $10^2$ organisms and another test tube was inoculated with $10^6$ organisms. Samples were obtained from each test tube to determine concentrations before incubation. Samples were diluted and plated out using sodium chloride serial dilution blanks and poured with Standard Methods Agar (SMA). The plates and simulated urine tubes were incubated at 37° Centigrade for 24 hours. After 24 hours, a sample was obtained from each simulated urine test tube again to determine the number of bacteria. The samples were diluted and plated using SMA and again incubated. The results were counted and recorded. In the test tube inoculated with $10^2$ organisms, the tube had bacterial growth which was too numerous to count (TNTC) at 0 dilutions and at $10^{-1}$ dilutions. After the incubation period, the test tube at $10^{-1}$ dilutions had growth too numerous to count; $10^{-2}$ dilutions had growth too numerous to count; $10^{-3}$ dilutions had growth too numerous to count; and $10^{-4}$ dilutions had $1.31 \times 10^6$ organisms.

The tube inoculated with $10^6$ organisms at $10^{-3}$ dilutions had growth too numerous to count; at $10^{-4}$ dilutions had growth of $2.43 \times 10^8$ organisms; and at $10^{-5}$ dilutions had growth of $3.9 \times 10^6$ organisms per milliliter. After incubation, the test tube had at $10^{-4}$ dilutions growth too numerous to count; $10^{-5}$ dilutions had growth $4.6 \times 10^6$ organisms per milliliter; $10^{-6}$ dilutions had growth $5 \times 10^6$ organisms per milliliter.

The results of the experiment showed that the simulated urine could support growth of E. coli 26 up to $10^6$ organisms per milliliter. The growth in the simulated urine was observed to undergo a 3 log increase within 24 hours.

EXAMPLE 2

The experiment herein was conducted to evaluate the inorganic peroxide, sodium perborate ($NaBO_3.4H_2O$) for its biocidal activity in urine. A titration of the samples was performed to determine the percentage by volume of hydrogen peroxide present both before and after incubation of each sample with E. coli as the challenge bacteria. Samples of sodium perborate in filtered urine were titrated to determine the percent active hydrogen peroxide present. Three varying amounts of sodium perborate were added to three test tubes each containing 25 milliliters of urine. To a first test tube, 0.75 grams of sodium perborate were added to 25 milliliters of urine which provided 0.3% active hydrogen peroxide. To a second test tube was added 0.225 grams of sodium perborate in 25 milliliters of urine to provide a 0.09% active hydrogen peroxide. To a third test tube, 0.075 grams of sodium perborate were added to 25 milliliters of urine to provide a 0.03% active hydrogen peroxide. The samples were allowed to mix thoroughly and react. The test tubes were titrated against sodium thiosulfate $Na_2S_2O_3$, using standard $H_2O_2$ titrating techniques and the results of $H_2O_2$ activity recorded.

An E. coli inoculum was prepared by transferring 1 cc of 18 to 24 hour culture of E. coli in TSB into 25 milliliters of filtered urine. The resultant mixture was incubated at 37° Centigrade for 18 to 24 hours. A growth was assumed to about $10^8$ organisms per milliliter.

The experiment was conducted by preparing test tubes with sodium perborate and 25 milliliters of filtered urine to initially provide 0.3%, 0.09%, and 0.03% hydrogen peroxide. The samples were allowed to react and an E. coli inoculum in a 1 to 100 dilution of $10^8$ culture in urine was used to inoculate each test tube. The inoculum size was about 0.25 milliliters. The inoculum was added to all three tubes containing sodium perborate, plus a control test tube containing the urine without the sodium perborate.

The samples in the challenge test tubes were diluted $10^{-1}$ through $10^{-4}$ and poured with SMA. The pour plates were incubated at 37° for 24 to 48 hours and the resultant plates counted and recorded. The samples were then weighed and titrated to determine the remaining active hydrogen peroxide in each tube.

The characterization of the filtered urine that was tested had the following characteristics: specific gravity, 1.020; pH, 7; nitrite, negative; protein, negative; glucose, normal; ketones, negative; urobilin, normal; bilirubin, negative; and blood, negative.

For the 0.3% hydrogen peroxide test tube, the bacteria was effectively killed after about 5 minutes. For the 0.09% hydrogen peroxide test tube, there was an effective kill of the bacteria after about 15 minutes. For the 0.03% hydrogen peroxide test tube, there was an effective kill of the bacteria after about 60 minutes.

The experiment performed herein showed that the sodium perborate rapidly killed E. coli in urine and that 0.3% hydrogen peroxide by volume reduced the bacterial load by 4 logs in 5 minutes, and the 0.03% hydrogen peroxide by volume reduced the load of bacteria by 4 logs in 60 minutes. Such a 4 log reduction translates to a 99.99% reduction in bacteria in the sample. Therefore, this experiment shows that the sodium perborate is an effective bactericidal agent in urine against E. coli at the concentrations and for the times indicated in this experiment.

EXAMPLE 3

The experiments performed in this example were conducted to evaluate sodium perborate tablets containing an ethylenediaminetetra-acetic acid (EDTA) as a buffer for the prevention of salt precipitation in urine. The tablets also contained magnesium stearate as a mold lubricant.

The experiments in this Example 3 were performed in substantially the same manner as the experiment set forth in Example 2, but the tablets were placed in a simulated urine. Titrations were performed to determine percent active peroxide available.

Three separate pairs of sodium perborate tablets were evaluated in an experiment performed substantially in the manner as the experiment set forth in Example 4. The first pair of tablets contained 2.5% EDTA, 0.3% magnesium stearate, and the remainder sodium perborate. The tablets were formed in a 10 ton press using 15,000 psi and subsequently spray coated with 6 coats of cellulose nitrate lacquer. The two tablets had a total combined weight of 20.20 grams. The two tablets for the second test were made in the same manner as the two tablets for the first test with the exception that 5% EDTA was used. The two tablets had a combined weight of 20.05 grams. The two tablets for the third test were formed in the same manner as the two tablets for the first with the exception that 7.5% by weight EDTA was used and the two tablets weighed 19.93 grams.

Figure 4:
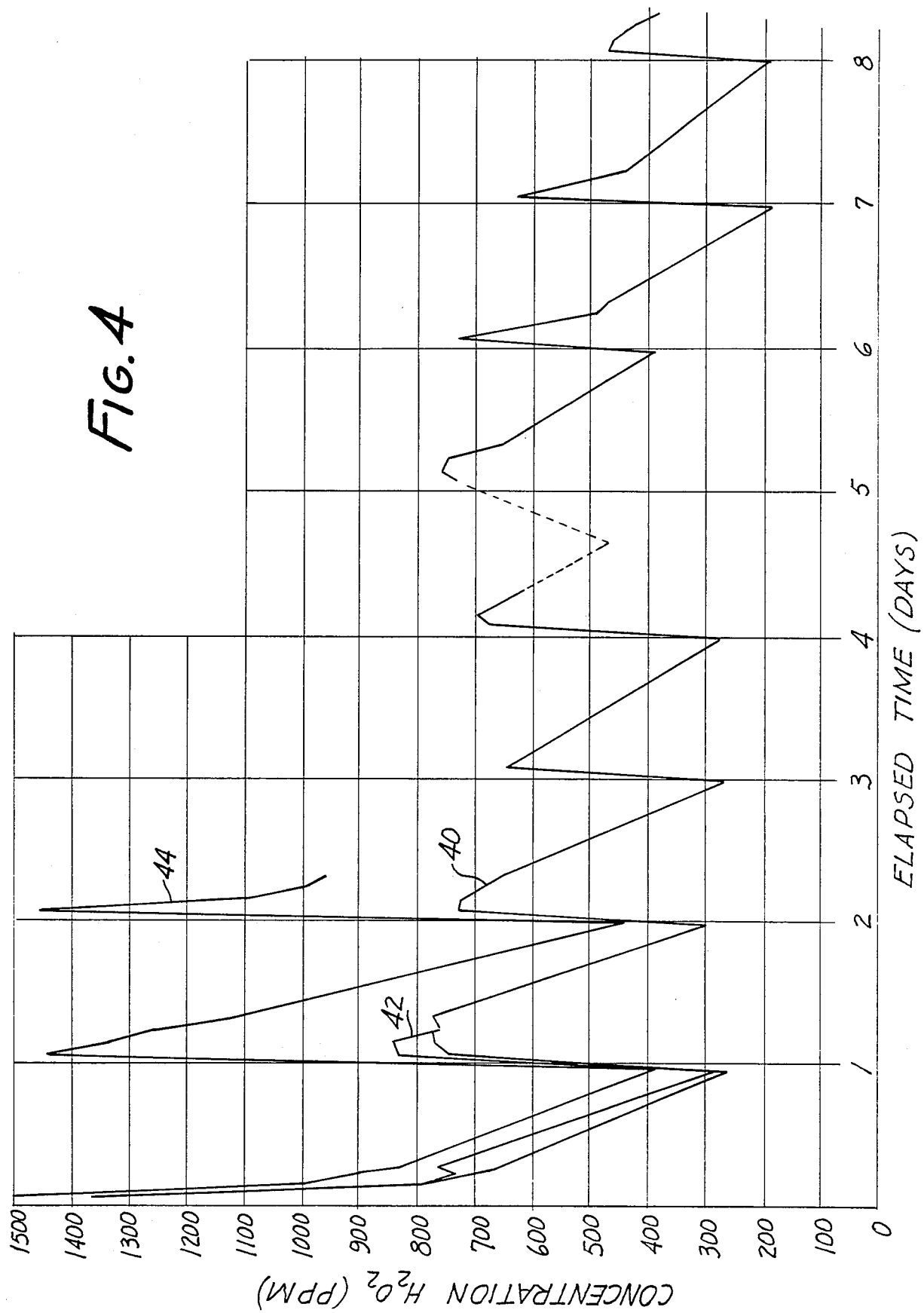
FIG. 4 is a plot of a series of curves illustrating the dissolution of tablets in simulated urine.

The results of the experiment are shown in FIG. 4 which represents a graph of the available hydrogen peroxide in parts per million over time in days. The line 40 represents the two tablets in the first experiment containing 2.5% EDTA, line 42 represents the two tablets containing 5.0% EDTA, and line 44 represents the tablet in the third experiment containing 7.5% EDTA. The dashed portion of curve 40 is a schematic interpolation of readings during the indicated time period as no direct measurements of $H_2O_2$ concentration were made.

The graph illustrates that a stable tablet can be formulated for release of $H_2O_2$ over a preselected time of anticipated catheterization for a patient using a buffered hydrogen peroxide generating tablet.

EXAMPLE 4

The experiment in this example was conducted to evaluate tablets of sodium perborate. A continuous drip diffusion system was employed whereby a filtered pooled human urine was drained drop-wise into a container wherein the tablets were placed. Titrations were performed to determine the percent active hydrogen peroxide present in the chamber. The average flow rate of the urine into the drainage bag was 48 milliliters per hour.

In this experiment, four different evaluations were conducted. In the first evaluation, two tablets were used which contained 0% EDTA; in the second evaluation, the tablets contained 2.5% EDTA; in the third evaluation, the tablets contained 5% EDTA; and in the fourth evaluation, the tablets contained 7.5% EDTA. In these experiments, the control tablets (no EDTA) were ⅞ of an inch in diameter and provided an effective available surface area for the two tablets of about 1.203 square inches. The tablets containing EDTA were all one inch in diameter and provided an available surface area for each two tablets of about 1.57 square inches. The two tablets containing 2.5% EDTA had a combined weight of 20.08 grams. The two tablets containing 5% EDTA had a total combined weight of 19.84 grams. The two tablets containing 7.5% EDTA had a combined total weight of 20.42 grams. The two tablets containing no EDTA had a combined total weight of 14.77 grams.

Figure 5:
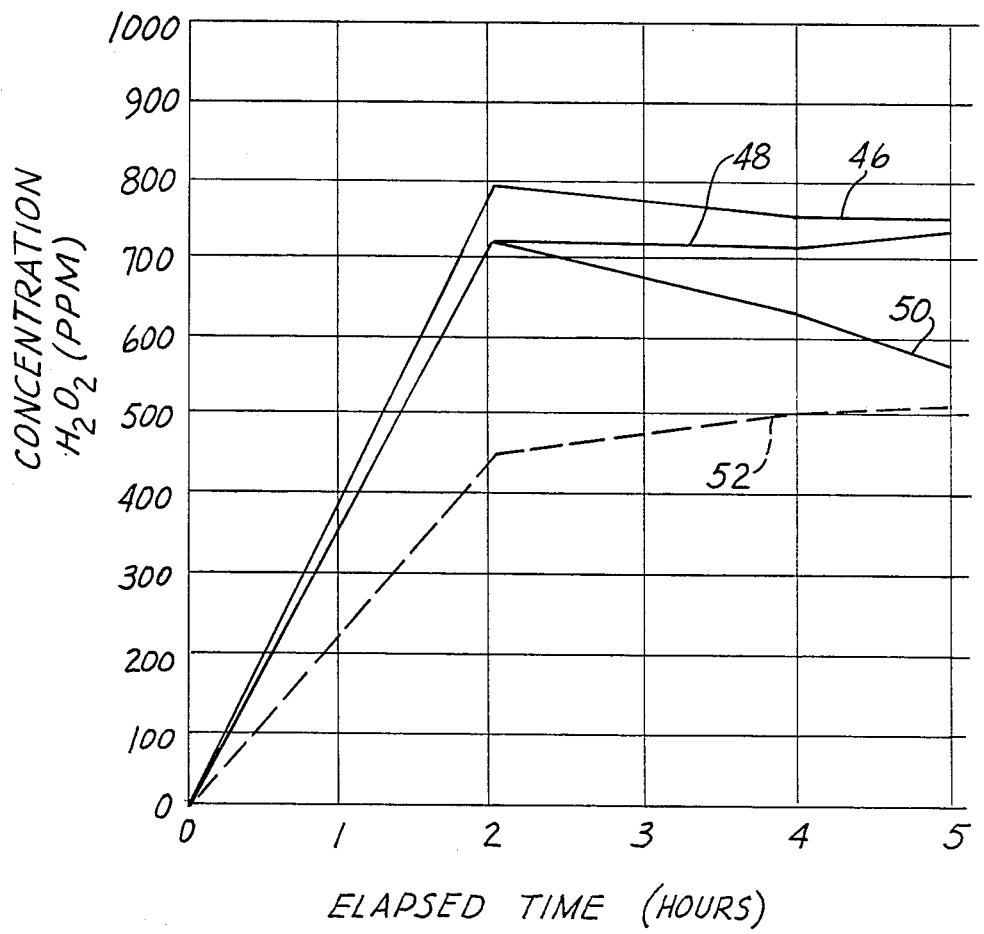
FIG. 5 is a plot of a series of curves illustrating the active $H_2O_2$ over time for tablets in urine.

The results of the experiments are shown in the graph in FIG. 5 which shows a plot of percentage available hydrogen peroxide in parts per million against time in hours. The line 46 represents the two tablets containing 2.5% EDTA, line 48 represents the two tablets containing 5% EDTA, line 50 represents the two tablets containing 7.5% EDTA, and line 52 represents the two control tablets containing no EDTA.

FIG. 5 illustrates that a constant rate or release of $H_2O_2$ in urine can be obtained for a tablet which includes a buffer agent. The control tablet also illustrates that the $H_2O_2$ generating tablet is effective in providing an effective $H_2O_2$ concentration over time in urine.

EXAMPLE 5

The experiment in this example was conducted to further investigate the antimicrobial activity of sodium perborate tablets on S. aureus and E. coli. These challenge bacteria were selected as they are frequently encountered in urinary tract infections and representative of gram negative and gram positive bacteria.

A solution was prepared containing about 0.05% active hydrogen peroxide in filtered urine by dissolving a tablet containing 95% sodium perborate and 5% sodium benzoate as a mold release agent. A culture of each bacteria was developed by obtaining an 18 to 24 hour culture of E. coli in trypticase soya broth (TSB) and an 18 to 24 hour culture of S. aureus in TSB was also made.

The initial available hydrogen peroxide from the sodium perborate solution was determined by titration. The urine alone as a control had a pH of about 6, and the urine plus sodium perborate had a pH of about 8. The available hydrogen peroxide in the urine solution was about 0.044% by volume.

Twenty-five milliliters of the sodium perborate solution was placed into two sterile flasks. The bacterial cultures were spun down in 5 milliliter aliquots and resuspended in 9 milliliters of sodium chloride solution. The solutions were diluted 1:10 for use as a challenge inoculum. The flasks were inoculated by placing 0.2 milliliters of the challenge inoculum per flask. The flask were shaken and incubated at 32° Centigrade. The test flasks were tested at 5, 15, 30, 45, and 60 minutes.

The samples taken from each flask were one milliliter aliquots which were placed into catalase neutralizer tubes and thereafter into sodium chloride for dilutions of $10^{-1}$ to $10^{-4}$. Plates were poured with SMA and the poured plates were incubated at 37° Centigrade for 24 to 48 hours. The plates were counted and the counts recorded. The results of the experiments are shown in the following table.

TABLE 1

| Sample Time | | E. coli Control | E. coli NaBO$_3$ | S. aureus Control | S. aureus NaBO$_3$ |
|---|---|---|---|---|---|
| 5 Minutes | $10^{-1}$ | TNTC* | TNTC | TNTC | TNTC |
| | $10^{-2}$ | TNTC | TNTC | TNTC | TNTC |
| | $10^{-3}$ | TNTC | TNTC | TNTC | TNTC |
| | $10^{-4}$ | $6.5 \times 10^6$ | $1.06 \times 10^6$ | $2 \times 10^6$ | $2.76 \times 10^6$ |
| 15 Minutes | $10^{-1}$ | —*** | TNTC | — | TNTC |
| | $10^{-2}$ | — | TNTC | — | TNTC |
| | $10^{-3}$ | — | TNTC | — | TNTC |
| | $10^{-4}$ | — | $6.2 \times 10^5$ | — | $1.44 \times 10^6$ |
| 30 Minutes | $10^{-1}$ | TNTC | TNTC | TNTC | TNTC |
| | $10^{-2}$ | TNTC | TNTC | TNTC | TNTC |
| | $10^{-3}$ | TNTC | $8.6 \times 10^4$ | TNTC | TNTC |
| | $10^{-4}$ | $9.6 \times 10^5$ | $1.0 \times 10^5$ | $2.25 \times 10^6$ | $6.3 \times 10^5$ |
| 45 Minutes | $10^{-1}$ | — | TNTC | — | TNTC |
| | $10^{-2}$ | — | $7.0 \times 10^3$ | — | TNTC |
| | $10^{-3}$ | — | $4 \times 10^3$ | — | TNTC |
| | $10^{-4}$ | — | $1 \times 10^4$ | — | $3.7 \times 10^5$ |
| 60 Minutes | $10^{-1}$ | TNTC | NC** | TNTC | TNTC |
| | $10^{-2}$ | TNTC | NC | TNTC | TNTC |
| | $10^{-3}$ | TNTC | NC | TNTC | $6.2 \times 10^4$ |
| | $10^{-4}$ | $7.6 \times 10^5$ | NC | $1.15 \times 10^4$ | |

*Too numerous to count
**No count - Less than 10 colonies/ml
***—Sample not taken As can be seen from the above table, the E. coli was reduced within 60 minutes and within 45 minutes there was a reduction of two logs with 0.04% available hydrogen peroxide. The S. aureus appeared to be more resistant and required 60 minutes for a two log reduction at 0.04% available hydrogen peroxide. The results show that the system herein does offer effective bactericidal and bacteristatic activity against both gram negative organisms (E. coli) and gram positive organism (S. aureus).

EXAMPLE 6

The experiment herein was conducted to determine the diffusion of sodium perborate tablets which utilize sodium benzoate or magnesium stearate as a mold lubricant and tablets which use boric acid as a buffering agent. The tablets all were tableted using sodium perborate and coated with a lacquer coating of a nitrocellulose base lacquer. The tablets were placed in a urinary drainage bag which was fed with a continuous drip of simulated urine to simulate actual use.

In one experiment herein, sodium perborate tablets with sodium benzoate having a combined weight of 14.66 grams for two tablets were placed in a urinary drainage bag. The tablets had a diameter of 2.3 centimeters and a height of 1.1 centimeters. In a second experiment, sodium perborate tablets with magnesium stearate and 5% boric acid and having a combined weight for two tablets of 31.47 grams, tablet diameter of 2.6 centimeters and a tablet height of 1.9 centimeters were placed in a urinary drainage bag.

Figure 6:
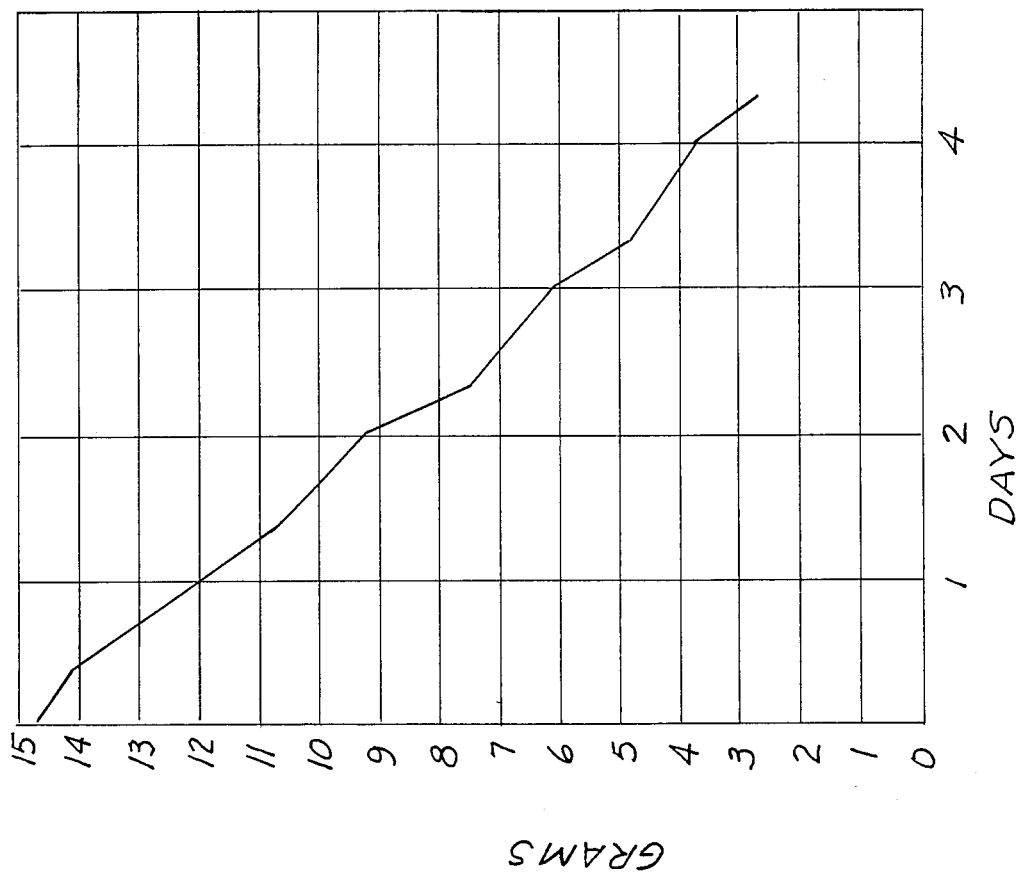
FIG. 6 is a plot of a curve illustrating the dissolution of a tablet in simulated urine.

The results of the study are represented in FIG. 6 wherein it is shown that the weight loss of the tablets was fairly uniform. FIG. 6 shows the curve which represents the weight loss of the sodium perborate/sodium benzoate nitrocellulose lacquer coated tablets over time. The curve shown in FIG. 6 is a plot of the weight of the tablets versus time in days. As can be seen from the graph, there is a steady dissolution of the tablets in the simulated urine.

Figure 7:
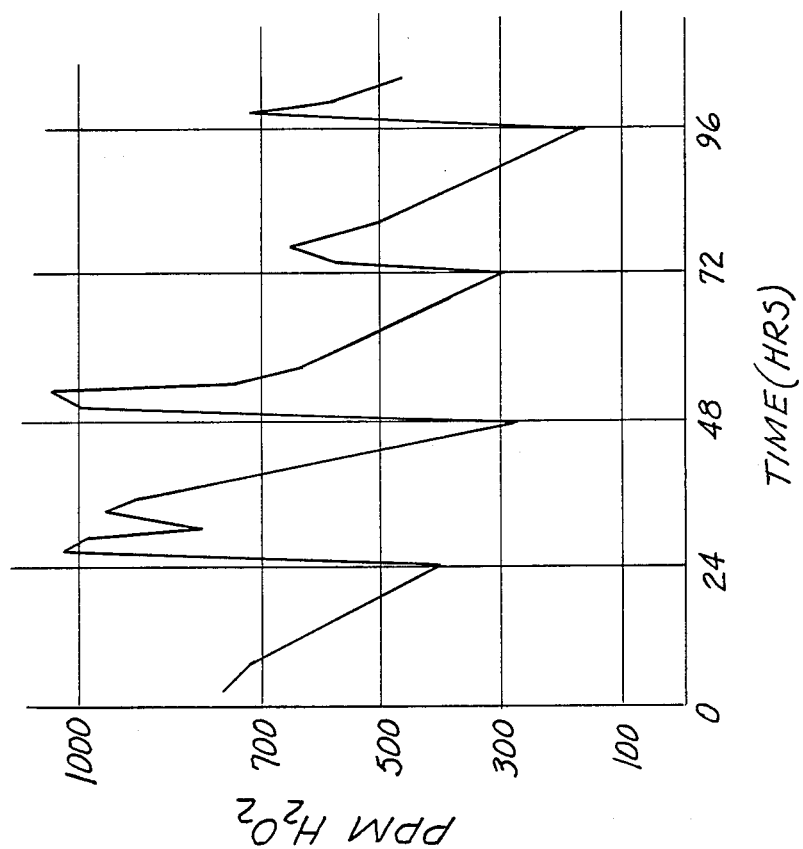
FIG. 7 is a plot of a curve for a tablet illustrating the effective $H_2O_2$ upon dissolution.

FIG. 7 shows the results of a dissolution of the sodium perborate/sodium benzoate lacquer coated tablets as a plot of available hydrogen peroxide in parts per million $H_2O_2$ versus time in hours.

FIG. 8 shows the results of the sodium perborate/boric acid/magnesium stearate nitrocellulose lacquer coated tablets over an eight day period. As can be seen from FIG. 8, the available hydrogen peroxide in parts per million is plotted against time in days. The dashed portion of the curve shown in FIG. 8 is a schematic interpolation of readings during the indicated time as no direct measurements of $H_2O_2$ concentration were made. As can be seen, the tablets which were followed for eight days provided an average peroxide level which was in excess of 0.06% which is generally an acceptable level to provide microbiocidal activity. To provide a microbiocidal level, it is preferable that the tablets be provided with a hydrogen peroxide generating composition which will produce hydrogen peroxide at a level of 0.03% to 0.15% hydrogen peroxide by volume. A 0.1% hydrogen peroxide presence in a body fluid is most preferred as it provides an efficient kill of microorganisms in a short time period.

The assembly herein which includes the placement of hydrogen peroxide releasing tablets in a body fluid collection reservoir, which tablets are coated to release a substantially constant rate of hydrogen peroxide at a concentration sufficient to kill microorganisms present in the collected body fluid, provides an assembly which prevents or inhibits the growth of bacteria and other microorganisms. The assembly is easily used and requires little or no attention from a nursing staff while performing its intended bacteristatic and bactericidal activity. The bacteristatic and bactericidal activity provided by the system can reduce the incidence of infections and thus aid in the reduction of hospital stays and costs.

We claim:

1. In a body fluid collection reservoir, an improvement comprising:
   a tablet in the reservoir, which tablet upon encountering the body fluid dissolves to produce hydrogen peroxide, which tablet is partially coated with a nondissolving coating leaving a fixed surface area uncoated and exposed to the body fluid, which fixed surface area remains substantially constant as the tablet dissolves in the body fluid.

2. A body fluid collection reservoir as recited in claim 1 wherein the uncoated surface area is of a size sufficient to provide a substantially constant rate of release of hydrogen peroxide to the body fluid in an amount sufficient for inhibiting the growth of microorganisms in the body fluid.

3. A body fluid collection reservoir as recited in claim 2 wherein the surface area is of a size sufficient to provide hydrogen peroxide in the body fluid in an amount sufficient to kill microorganisms present in the body fluid.

4. A body fluid collection reservoir as recited in claim 1 wherein the tablet comprises a hydrogen peroxide generating composition selected from the group consisting of sodium perborate, sodium percarbonate, oxone peroxymonosulfate, and urea peroxide.

5. A body fluid collection reservoir as recited in claim 4 wherein the tablet comprises sodium perborate.

6. A body fluid collection reservoir as recited in claim 1 wherein the coating on the tablet comprises a body fluid insoluble compound selected from the group consisting of nitrocellulose base lacquer, epoxy, urethane, cellulose acetate, low density polyethylene, polymethylmethacrylate, polypropylene, silicone, vinyl, and polycarbonate.

7. A body fluid collection reservoir as recited in claim 6 wherein the coating comprises nitrocellulose base lacquer.

8. A body fluid collection reservoir as recited in claim 1 wherein the tablet further comprises a release agent for permitting the tablet to be removed from a mold in which the tablet is made.

9. A body fluid collection reservoir as recited in claim 8 wherein the release agent is selected from the group consisting of stearic acid, boric acid, zinc stearate, sodium benzoate, and magnesium stearate.

10. A body fluid collection reservoir as recited in claim 1 wherein the tablet and coating are bonded together such that the body fluid cannot appreciably flow between the tablet and the coating.

11. A body fluid collection reserovir as recited in claim 1 wherein the tablet further comprises a buffering agent for maintaining the pH in the collected body fluid at about a pH of 6 to 7.

12. A body fluid collection reservoir as recited in claim 1 wherein the tablet further comprises a binding agent for preventing lamination.

13. A body fluid collection reservoir as recited in claim 12 wherein the binding agent is selected from the group consisting of polyvinylpyrrolidone, magnesium silicate, and methylcellulose.

14. A body fluid collection reservoir as recited in claim 1 wherein the improvement further comprises a second tablet in the reservoir comprised of the same material as the first tablet and wherein the first and second tablets provide an uncoated surface area which when exposed to the body fluid provides a sufficient amount of hydrogen peroxide to inhibit microorganism growth in the collected body fluid.

15. A body fluid collection reservoir as recited in claim 14 wherein the surface area of the two tablets is sufficient to provide a range of about 0.03–0.15% by weight hydrogen peroxide in the body fluid.

16. A body fluid collection reservoir as recited in claim 14 wherein each of the tablets comprises sodium perborate, and each tablet is about one inch in diamter and weighs about 10 grams.

17. A urinary drainage and collection assembly for collecting urine drained from a patient and for inhibiting microbial growth in the collected urine, the assembly comprising:
   a urinary catheter for implanting in a patient's urinary tract for draining urine from the patient;
   a collection reservoir in fluid communication with the catheter for collecting urine drained from the patient; and
   a tablet in the reservoir, which tablet dissolves in urine to produce hydrogen peroxide and which tablet is partially coated with a urine insoluble coating, leaving a sufficient surface area uncoated on the tablet, which surface area remains substantially constant as the tablet dissolves in the collected urine to provide a uniform release of hydrogen peroxide in an amount sufficient for inhibiting microbial growth in the collected urine.

18. A urinary drainage and collection assembly as recited in claim 17 further comprising two tablets in the reservoir, which two tablets provide a combined surface area to provide about 0.03 percent to about 0.15 percent by weight hydrogen peroxide in the collected urine.

19. A urinary drainage and collection assembly as recited in claim 18 wherein each tablet comprises sodium perborate and the coating comprises a nitrocellulose base lacquer.

20. A urinary drainage and collection assembly as recited in claim 19 wherein each of the tablets contains about 9.5 to about 10 grams of sodium perborate and the total uncoated surface area for the two tablets comprises about 1.57 square inches.

21. A method for inhibiting the growth of microbes in a collected body fluid, the method comprising the step of:
   introducing to a reservoir for collection of body fluid a tablet which is capable of dissolving in such body fluid and releasing hydrogen peroxide, the tablet being partially coated with an insoluble coating leaving uncoated a surface area of the tablet, which surface area remains substantially constant as the tablet dissolves and which is sufficient for releasing sufficient hydrogen peroxide for inhibiting microbial growth in the collected body fluid.

22. A method as recited in claim 21 wherein the tablet introduced comprises a hydrogen peroxide generating composition selected from the group consisting of sodium perborate, sodium percarbonate, oxone peroxymonosulfate, and urea peroxide.

23. A method as recited in claim 21 wherein the coating on the tablet comprises a body fluid insoluble compound selected from the group consisting of nitrocellulose base lacquer, epoxy, urethane, cellulose acetate, low density polyethylene, polymethylmethacrylate, polypropylene, silicone, vinyl and polycarbonate.

24. A method as recited in claim 22 wherein the tablets introduced have a combined uncoated surface area sufficient to provide a substantially consistent rate of release of hydrogen peroxide to provide from about 0.03 percent to about 0.15 percent by weight hydrogen peroxide in the collected body fluid.

25. A method as recited in claim 24 wherein the tablets introduced have a combined uncoated surface area of about 1.57 square inches.

* * * * *